US009227895B2

(12) United States Patent
Tirmizi et al.

(10) Patent No.: US 9,227,895 B2
(45) Date of Patent: Jan. 5, 2016

(54) METHODS AND APPARATUS FOR PRODUCING ALCOHOLS FROM SYNGAS

(75) Inventors: Shakeel H. Tirmizi, Matawa, NJ (US);
Robert E. Klepper, Arvada, CO (US);
Francis M. Ferraro, Westminster, CO (US)

(73) Assignee: ALBEMARLE CORPORATION, Baton Rouge, LA (US)

( * ) Notice: Subject to any disclaimer, the term of this patent is extended or adjusted under 35 U.S.C. 154(b) by 1933 days.

(21) Appl. No.: 12/166,212

(22) Filed: Jul. 1, 2008

(65) Prior Publication Data

US 2009/0018372 A1 Jan. 15, 2009

Related U.S. Application Data

(60) Provisional application No. 60/948,657, filed on Jul. 9, 2007.

(51) Int. Cl.
*C07C 29/80* (2006.01)
*C07C 29/151* (2006.01)
*C07C 29/76* (2006.01)

(52) U.S. Cl.
CPC ............. *C07C 29/1518* (2013.01); *C07C 29/76* (2013.01)

(58) Field of Classification Search
USPC ......................................... 568/700, 708, 916
See application file for complete search history.

(56) References Cited

U.S. PATENT DOCUMENTS

| | | |
|---|---|---|
| 4,171,461 A | 10/1979 | Bartish |
| 4,233,466 A | 11/1980 | Fiato |
| 4,253,987 A | 3/1981 | Fiato |
| 4,277,634 A | 7/1981 | Walker |
| 4,371,724 A | 2/1983 | Lin et al. |
| 4,374,285 A | 2/1983 | Lin et al. |
| 4,405,343 A | 9/1983 | Othmer |
| 4,409,405 A | 10/1983 | Lin et al. |
| 4,424,384 A | 1/1984 | Lin et al. |
| 4,607,055 A | 8/1986 | Grazioso et al. |
| 4,607,056 A | 8/1986 | Grazioso et al. |
| 4,616,040 A | 10/1986 | Grazioso et al. |
| 4,628,113 A | 12/1986 | Current |
| 4,661,525 A | 4/1987 | Grazioso et al. |
| 4,675,344 A | 6/1987 | Conway et al. |
| 4,692,432 A * | 9/1987 | Tedder ........................ 568/916 |
| 4,749,724 A | 6/1988 | Quarderer et al. |
| 4,752,622 A | 6/1988 | Stevens |
| 4,752,623 A | 6/1988 | Stevens |
| 4,752,626 A | 6/1988 | Hoye et al. |
| 4,762,858 A | 8/1988 | Hucul et al. |
| 4,775,696 A | 10/1988 | Prada-Silva et al. |
| 4,824,869 A | 4/1989 | Prada-Silva et al. |
| 4,825,013 A | 4/1989 | Quarderer et al. |
| 4,886,772 A | 12/1989 | Prada-Silva et al. |
| 4,980,380 A | 12/1990 | Wong et al. |
| 5,451,558 A | 9/1995 | Campbell et al. |
| RE35,377 E | 11/1996 | Steinberg et al. |
| 5,990,039 A | 11/1999 | Paul et al. |
| 6,133,328 A | 10/2000 | Lightner |
| 6,156,693 A | 12/2000 | Song et al. |
| RE37,046 E | 2/2001 | Hildinger et al. |
| 6,248,796 B1 | 6/2001 | Jackson et al. |
| 6,281,158 B1 | 8/2001 | Gabrielov et al. |
| 6,383,974 B1 | 5/2002 | Ishida et al. |
| 6,387,842 B1 | 5/2002 | Wegman et al. |
| 6,387,963 B1 | 5/2002 | Fitzpatrick |
| 6,444,712 B1 | 9/2002 | Janda |
| 6,451,729 B1 | 9/2002 | Song et al. |
| 6,455,748 B2 * | 9/2002 | Janssen et al. ................ 585/638 |
| 6,616,909 B1 | 9/2003 | Tonkovich et al. |
| 6,706,770 B2 | 3/2004 | Patel et al. |
| 6,753,352 B2 | 6/2004 | Seiki et al. |
| 6,753,353 B2 | 6/2004 | Jackson et al. |
| 6,762,332 B2 | 7/2004 | Lange |
| 6,767,375 B1 | 7/2004 | Pearson |
| 6,818,198 B2 | 11/2004 | Singh et al. |
| 6,858,048 B1 | 2/2005 | Jimeson et al. |
| 6,863,878 B2 | 3/2005 | Klepper |
| 6,875,794 B2 | 4/2005 | Seiki et al. |
| 6,894,080 B2 | 5/2005 | Seiki et al. |
| 6,919,488 B2 | 7/2005 | Melnichuk et al. |
| 6,981,994 B2 | 1/2006 | Drnevich et al. |
| 6,991,769 B2 | 1/2006 | Kaneko et al. |
| 7,008,967 B2 | 3/2006 | Keyser et al. |
| 7,048,772 B1 | 5/2006 | Bedetti |

(Continued)

FOREIGN PATENT DOCUMENTS

| | | |
|---|---|---|
| EP | 1860088 | 11/2007 |
| EP | 1923380 | 5/2008 |

OTHER PUBLICATIONS

Hironori Arakawa et al., "Selective Synthesis of Ethanol Over Rh—Ti—Fe—Ir/SiO2 Catalyst at High Pressure Syngas Conversion", Chemistry Letters, pp. 881-884, Mar. 11, 1985.

Division of Chemical Reaction Engineering, KTH-Kungl. Tekniska Högskolan, "Torrefied Wood an Alternative to Charcoal for Reducing Deforestation", http://hem.fyristorg.com/zanzi/torrefaction.html, Feb. 2001.

John L. Falconer et al., "Zeolite Membrane Research", http://www.colorado.edu/che/FalcGrp/research/zeolite.html (1996).

Jianli Hu et al., "Conversion of Biomass-Derived Syngas to Alcohols and C2 Oxygenates Using Supported Rh Catalysts in a Microchannel Reactor", Catalysis Today, vol. 120, pp. 90-95, Sep. 6, 2006.

(Continued)

*Primary Examiner* — Sudhakar Katakam
*Assistant Examiner* — Pancham Bakshi
(74) *Attorney, Agent, or Firm* — Nathan C. Dunn; James A. Jubinsky; Marcy M. Hoefling

(57) ABSTRACT

Methods and apparatus for producing alcohols from syngas are disclosed herein. In some variations, syngas is catalytically converted to alcohols. The alcohols can be subjected to drying to produce an intermediate alcohol product, followed by distilling the intermediate product to produce a purified ethanol product for use in liquid fuels.

27 Claims, 3 Drawing Sheets

(56) References Cited

U.S. PATENT DOCUMENTS

| | | |
|---|---|---|
| 7,091,251 B2 | 8/2006 | Guillard et al. |
| 7,144,923 B2 | 12/2006 | Fitzpatrick |
| 7,169,821 B2 | 1/2007 | Branson |
| 7,176,160 B2 | 2/2007 | Espinoza et al. |
| 7,192,987 B2 | 3/2007 | Van Egmond et al. |
| 7,196,239 B2 | 3/2007 | Van Egmond et al. |
| 7,214,721 B2 | 5/2007 | Eastland |
| 7,279,019 B2 | 10/2007 | Weedon |
| 7,297,236 B1 | 11/2007 | Vander Griend |
| 2002/0177741 A1* | 11/2002 | Allison et al. ............... 568/840 |
| 2004/0018423 A1* | 1/2004 | Bollito et al. ............... 429/127 |
| 2005/0107481 A1* | 5/2005 | Janssen et al. ............... 518/726 |
| 2006/0009537 A1 | 1/2006 | Iordache-Cazana et al. |
| 2007/0004809 A1 | 1/2007 | Lattner et al. |
| 2007/0161717 A1 | 7/2007 | Hu et al. |
| 2007/0205092 A1 | 9/2007 | Klepper |

OTHER PUBLICATIONS

Masaru Ichikawa et al., "Mechanism of Syngas Conversion Into C2-Oxygenates Such as Ethanol Catalysed on a SiO2-Supported Rh—Ti Catalyst", J. Chem. Soc., Chem. Commun., pp. 321-323 (1985).

Hongtao Ma et al., "Temperature-Programmed Surface Reaction Study on C2-Oxygenate Synthesis Over SiO2 and Nanoporous Zeolitic Material Supported Rh—Mn Catalysts", Surf. Interface Anal., vol. 32, pp. 224-227, Jan. 8, 2001.

C.B. Murchison et al., "Mixed Alcohols From Syngas Over Moly Catalysts", Proc. 9th Intern. Cong. Catal., vol. 2, pp. 626-633 (1988).

G.K. Pearce, "Pervaporation vs. Distillation. A Comparative Costing for Alcohol Dehydration", Proc. Int. Conf. Pervaporation Processes, ISBN:0939997088, pp. 278-296 (1989).

S. Phillips et al., "Thermochemical Ethanol via Indirect Gasification and Mixed Alcohol Synthesis of Lignocellulosic Biomass", NREL Technical Report/TP-510-41168 (Apr. 2007).

Jose G. Santiesteban et al., "Mechanism of C1-C4 Alcohol Synthesis Over Alkali/MoS2 and Alkali/Co/MoS2 Catalysts", Proc. 9th Intern. Cong. Catal., 2, 561-568 (1988).

P.L. Spath et al., Technical Report, "Preliminary Screening—Technical and Economic Assessment of Synthesis Gas to Fuels and Chemicals with Emphasis on the Potential for Biomass-Derived Syngas", NREL Report No. NREL/TP-510-34929, Dec. 2003.

G. Van Der Lee et al., "On the Selectivity of Rh Catalysts in the Formation of Oxygenates", Journal of Catalysis, vol. 98, pp. 522-529 (1986).

* cited by examiner

METHODS AND APPARATUS FOR PRODUCING ALCOHOLS FROM SYNGAS

PRIORITY DATA

This patent application claims priority under 35 U.S.C. §120 from U.S. Provisional Patent Application No. 60/948,657 for "Methods and Apparatus for Producing Alcohols from Syngas" which is hereby incorporated by reference herein for all purposes.

FIELD OF THE INVENTION

The present invention generally relates to processes for the conversion of carbonaceous feedstocks, such as cellulosic biomass, into synthesis gas, and to processes for the conversion of synthesis gas to products such as alcohols (e.g., ethanol).

BACKGROUND OF THE INVENTION

Ethanol and alcohol mixtures including ethanol may be used as fuels and fuel additives in place of petroleum-based products such as gasoline. Such use of alcohols can reduce the need to import petroleum. In addition, the substitution of alcohols for petroleum-based fuels and fuel additives can be particularly environmentally friendly when the alcohols are produced from feedstocks other than fossil fuels.

One synthetic route to alcohols is through catalytic processes for the conversion of syngas to alcohols. Syngas (or synthesis gas) is a mixture of monoxide (CO) and hydrogen ($H_2$). Generally, syngas may be produced from any carbonaceous material. In particular, biomass such as, for example, agricultural wastes, forest products, grasses, and other cellulosic material may be converted to syngas.

There exist a variety of conversion technologies to turn these feedstocks into syngas. Conversion approaches can utilize a combination of one or more steps comprising gasification, pyrolysis, steam reforming, and/or partial oxidation of a carbonaceous material.

Since the 1920s it has been known that mixtures of methanol and other alcohols can be obtained by reacting syngas over certain catalysts (Forzatti et al., *Cat. Rev.—Sci. and Eng.* 33(1-2), 109-168, 1991). Fischer and Tropsch observed around the same time that hydrocarbon-synthesis catalysts produced linear alcohols as byproducts (Fischer and Tropsch, *Brennst.-Chem.* 7:97, 1926).

However, improved methods and apparatus to convert syngas into alcohols, such as ethanol, are currently needed.

SUMMARY OF THE INVENTION

In some embodiments, the present invention provides a method of purifying one or more alcohols selected from the group consisting of methanol, ethanol, propanol, and butanol, the method comprising the steps of (a) drying an initial mixture comprising methanol, ethanol, propanol, butanol, and water to produce an intermediate product; and then (b) distilling the intermediate product to produce one or more purified alcohols.

In some embodiments, the invention provides a method of producing a purified alcohol selected from the group consisting of methanol, ethanol, propanol, and butanol, the method comprising the steps of:

(a) devolatilizing a carbon-containing feed material to form a gas phase and a solid phase in a devolatilization unit;

(b) passing the gas phase and the solid phase through a heated reaction vessel to form syngas;

(c) converting the syngas to a mixture comprising ethanol, methanol, propanol, butanol, and water;

(d) drying the mixture to produce an intermediate product; and (e) distilling the intermediate product to produce a purified alcohol.

The amount of ethanol in the initial mixture can be between about 25% and about 95% by weight. The amount of methanol in the initial mixture can be between about 0.1% and about 50% by weight. The amount of water in the initial mixture can be between about 1% and about 50% by weight.

The amount of water in the intermediate product can be less than about 5%, preferably less than about 0.5% by weight. In preferred embodiments, step (a) removes at least 75%, more preferably at least 95%, of the water present in the initial mixture.

In some embodiments, step (a) comprises passing the initial mixture through a membrane, such as a zeolite membrane. In some embodiments, step (a) comprises passing the initial mixture through a desiccant, such as (for example) a desiccant selected from the group consisting of $SiO_2$, CaO, $CaCO_3$, $CaCl_2$, $CuSO_4$, and $CaSO_4$. In some embodiments, step (a) comprises passing the initial mixture through a molecular sieve. Preferably, the molecular sieve has an effective pore size of less than about 5 Angstroms, such as about 3 Angstroms.

In some methods, one of the purified alcohols is ethanol. In other methods, one of the purified alcohols is 1-propanol and/or 1-butanol. The distilling step can produce a purified methanol product and a purified ethanol product; or a purified methanol product, a purified ethanol product, and a purified 1-propanol product; or some other combination of purified alcohols as may be desired.

In some embodiments, the ethanol concentration of the purified ethanol is between about 95% and about 99.9% by weight. In certain embodiments, the purified ethanol meets the ASTM D4806-07a specification for fuel ethanol.

Some methods further include powering an internal combustion engine, at least in part, with the one or more purified alcohols. Other methods can include combining the one or more purified alcohols with at least one other hydrocarbon, such as gasoline, thereby creating a liquid-fuel blend, which can be combusted.

This invention also describes apparatus for producing a purified alcohol selected from the group consisting of methanol, ethanol, propanol, and butanol, the apparatus comprising:

(a) means for devolatilizing a carbon-containing feed material to form a gas phase and a solid phase in a devolatilization unit;

(b) means for passing the gas phase and the solid phase through a heated reaction vessel to form syngas;

(c) means for converting the syngas to a mixture comprising ethanol, methanol, propanol, butanol, and water;

(d) means for drying the mixture to produce an intermediate product; and (e) means for distilling the intermediate product to produce a purified alcohol, wherein the apparatus is configured for the drying prior to the distilling.

In some embodiments, the apparatus includes a zeolite membrane, a desiccant, a molecular sieve, or some combination of these means for dehydration.

These and other embodiments, features, and advantages of the present invention will become more apparent to those skilled in the art when taken with reference to the following more detailed description of the invention in conjunction with the accompanying drawings that are first briefly described.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used herein, "$C_1$-$C_4$ alcohols" means one or more alcohols selected from methanol, ethanol, propanol, and butanol, including all known isomers of such compounds. While some embodiments are described in relation to high selectivities to ethanol, the invention can also be practiced in a manner that gives high selectivities to methanol, propanol, and/or butanol, or certain combinations of selectivities to methanol, ethanol, propanol, and butanol. "$C_2$-$C_4$ alcohols" means one or more alcohols selected from ethanol, propanol, and butanol, including all known isomers of such compounds.

Figure 1:
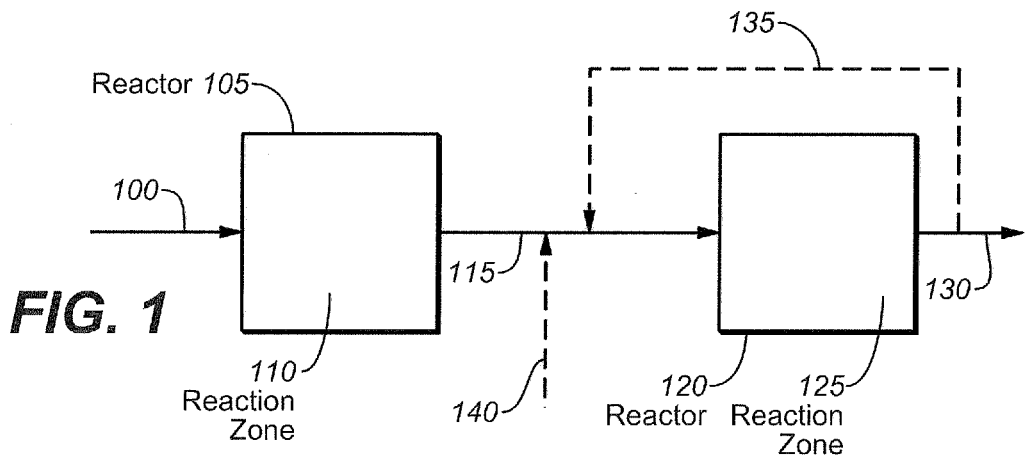
FIG. 1 shows a process flow for producing methanol and ethanol from syngas using two reactors in sequence, according to one variation.

Methods and apparatus for producing $C_1$-$C_4$ alcohols from syngas are disclosed herein. In some variations of these methods and apparatus, syngas is catalytically converted to methanol in a first reaction zone, and residual syngas from the first reaction zone is then catalytically converted to ethanol in a second reaction zone. Referring to FIG. 1, for example, in one variation a syngas feedstream 100 is introduced into a first reactor 105 comprising a first reaction zone 110. One or more catalysts in reaction zone 110 convert at least a portion of syngas feedstream 100 to methanol to provide an intermediate product stream 115 comprising at least a portion of the residual (unreacted) syngas from feedstream 100, methanol, and, in some variations, higher alcohols and/or other reaction products.

At least a portion of intermediate product stream 115 is introduced into a second reactor 120 comprising a second reaction zone 125. One or more catalysts in reaction zone 125 convert at least a portion of syngas from intermediate product stream 115 and/or at least a portion of methanol from intermediate product stream 115 to provide a product stream 130 comprising ethanol and, in some variations, methanol, higher alcohols, other reaction products, and/or unreacted syngas from intermediate product stream 115.

Various components of product stream 130 such as, for example, methanol, ethanol, alcohol mixtures (e.g., methanol, ethanol, and/or higher alcohols), water, and unreacted syngas may be separated out and (optionally) purified by the methods described herein or by conventional methods. Such methods may include, for example, distillation and membrane separation processes as well as drying or purifying with molecular sieves.

Syngas feedstream 100 may be produced in any suitable manner known to one of ordinary skill in the art from any suitable feedstock. In some variations, syngas feedstream 100 is filtered, purified, or otherwise conditioned prior to being introduced into reactor 105. For example, carbon dioxide, benzene, toluene, ethyl benzene, xylenes, sulfur compounds, metals, and/or other impurities or potential catalyst poisons may be removed from syngas feedstream 100 by conventional methods known to one of ordinary skill in the art.

In some variations, syngas feedstream 100 comprises $H_2$ and CO at a $H_2$/CO ratio having a value between about 0.5 to about 3.0, about 1.0 to about 1.5, or about 1.5 to about 2.0. The $H_2$/CO ratio in feedstream 100 can, in some variations, affect the yield of methanol and other products in reactor 105. The preferred $H_2$/CO ratio in such variations may depend on the catalyst or catalysts used in reactor 105 as well as on the operating conditions. Consequently, in some variations, the production and/or subsequent conditioning of syngas feedstream 100 is controlled to produce syngas having a $H_2$/CO ratio within a range desired to optimize, for example, production of methanol, ethanol, or both methanol and ethanol.

Syngas feedstream 100 may optionally be pressurized and/or heated by compressors and heaters (not shown) prior to entering reactor 105. In some variations, syngas feedstream 100 enters reactor 105 at a temperature of about 300° F. to about 600° F. and at a pressure of about 500 psig to about 2500 psig. In some embodiments, the temperature is between about 300° F. to about 400° F., about 400° F. to about 500° F., or about 500° F. to about 600° F. In some embodiments, the pressure is about 500 psig to about 1000 psig, about 1000 psig to about 2000 psig, or about 2000 psig to about 2500 psig.

Reactor 105 may be any type of catalytic reactor suitable for the conversion of syngas to methanol, alcohol mixtures comprising methanol, higher alcohols, and/or other products. Reactor 105 may, for example, be any suitable fixed-bed reactor. In some variations, reactor 105 comprises tubes filled with one or more catalysts. Syngas passing through the tubes undergoes catalyzed reactions to form methanol and, in some variations, higher alcohols or other products. In some embodiments, catalysis occurs within pellets or in a homogeneous phase.

Reactor 105 may operate, for example, at temperatures of about 400° F. to about 700° F. and at pressures of about 500 psig to about 2500 psig. In some embodiments, the temperature is between about 400° F. to about 500° F., about 500° F. to about 600° F., or about 600° F. to about 700° F. In some embodiments, the pressure is about 500 psig to about 1000 psig, about 1000 psig to about 2000 psig, or about 2000 psig to about 2500 psig.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst contact times can also be calculated by a skilled artisan and these times will typically also be in the range of 0.1-10 seconds, although it will be appreciated that it is certainly possible to operate at shorter or longer times.

The reactor for converting syngas into alcohols can be engineered and operated in a wide variety of ways. The reactor operation can be continuous, semicontinuous, or batch. Operation that is substantially continuous and at steady state is preferable. The flow pattern can be substantially plug flow, substantially well-mixed, or a flow pattern between these extremes. The flow direction can be vertical-upflow, vertical-downflow, or horizontal. A vertical configuration can be preferable.

The "reactor" can actually be a series or network of several reactors in various arrangements. For example, in some variations, the reactor comprises a large number of tubes filled with one or more catalysts.

Any suitable catalyst or combination of catalysts may be used in reactor 105 to catalyze reactions converting syngas to methanol and, optionally, to higher alcohols and/or other products. Suitable catalysts may include, but are not limited to, one or more of $ZnO/Cr_2O_3$, $Cu/ZnO$, $Cu/ZnO/Al_2O_3$, $Cu/ZnO/Cr_2O_3$, $Cu/ThO_2$, Co/Mo/S, Co/S, Mo/S, Ni/S, Ni/Mo/S, Ni/Co/Mo/S, Rh, Ti, Fe, Ir, and any of the foregoing in combination with Mn and/or V. The addition of basic promoters (e.g. K, Li, Na, Rb, Cs, and Fr) increases the activity and selectivity of some of these catalysts for alcohols. Basic promoters include alkaline-earth and rare-earth metals. Non-metallic bases can also serve as effective promoters, in some embodiments.

The catalyst phase can be a packed bed or a fluidized bed. The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In some variations, up to about 50% of CO in syngas feedstream 100 is converted to methanol in reaction zone 110. Intermediate product stream 115 output from reactor 105 may comprise, in some variations, about 5% to about 50% methanol, about 5% to about 50% ethanol, about 5% to about 25% CO, about 5% to about 25% $H_2$, and about 2% to about 35% $CO_2$, as well as other gases. In some embodiments, intermediate product stream 115 also comprises one or more higher alcohols, such as ethanol, propanol, or butanol.

The $H_2/CO$ ratio in intermediate product stream 115 can, in some variations, affect the yield of ethanol and other products in reactor 120. The preferred $H_2/CO$ ratio in such variations may depend on the catalyst or catalysts used in reactor 120 as well as on the operating conditions. The $H_2/CO$ ratio in intermediate product stream 115 can differ from that of feedstream 100 as a result of reactions occurring in reactor 105. In some variations, the $H_2/CO$ ratio of intermediate product stream 115 provides a higher ethanol yield in reactor 120 than would the $H_2/CO$ ratio of feedstream 100. In such variations, operation of reactor 105 to produce methanol, for example, improves the $H_2/CO$ ratio of the syngas fed to reactor 120 from the standpoint of ethanol yield in reactor 120.

In one example, feedstream 100 comprises syngas with an $H_2/CO$ ratio of about 1.5 to about 2, and the preferred $H_2/CO$ ratio for production of ethanol in reactor 120 is about 1. Operation of reactor 105 to produce methanol in this example depletes $H_2$ in the syngas to decreases the $H_2/CO$ ratio in intermediate product stream 115 to a value closer to 1 and thus improves the ethanol yield in reactor 120. In certain embodiments, the catalyst in reactor 105 is a Cu/ZnO/alumina catalyst.

Reactor 120 may be any type of catalytic reactor suitable for the conversion of syngas, methanol, and/or syngas plus methanol to ethanol and, optionally, to higher alcohols and/or other products. Reactor 120 may be any suitable fixed-bed reactor, for example. In some variations, reactor 120 comprises tubes filled with one or more catalysts. Syngas and/or methanol passing through the tubes undergoes surface catalyzed reactions to form ethanol and, in some variations, higher alcohols and/or other products.

While not intending to be bound by any particular theory, it is presently believed that the methanol may be converted to syngas and thence to ethanol, the methanol may be converted directly to ethanol via a homologation reaction, and/or the methanol may be converted to ethanol by other mechanisms.

Reactor 120 may operate, for example, at temperatures of about 500° F. to about 800° F. and at pressures of about 500 psig to about 2500 psig. In some embodiments, the temperature is between about 500° F. to about 600° F., about 600° F. to about 700° F., or about 700° F. to about 800° F. In some embodiments, the pressure is about 500 psig to about 1000 psig, about 1000 psig to about 2000 psig, or about 2000 psig to about 2500 psig.

Any suitable catalyst or combination of catalysts may be used in reactor 120 to catalyze reactions converting syngas, methanol, and/or syngas+methanol to ethanol and, optionally, to higher alcohols and/or other products. Suitable catalysts may include, but are not limited to, alkali/$ZnO/Cr_2O_3$, $Cu/ZnO$, $Cu/ZnO/Al_2O_3$, $CuO/CoO$, $CuO/CoO/Al_2O_3$, Mo/S, Co/Mo/S, Ni/S, Ni/Mo/S, Ni/Co/Mo/S, $Rh/Ti/SiO_2$, $Rh/Mn/SiO_2$, $Rh/Ti/Fe/Ir/SiO_2$, Rh/Mn/MCM-41, Cu, Zn, Rh, Ti, Fe, Ir, and mixtures thereof. The addition of basic promoters (e.g. K, Li, Na, Rb, Cs, and Fr) increases the activity and selectivity of some of these catalysts for ethanol or other $C_{2+}$ alcohols. Basic promoters include alkaline-earth and rare-earth metals. Non-metallic bases can also serve as effective promoters, in some embodiments.

In some embodiments, catalysts for reactor 120 can include one or more of $ZnO/Cr_2O_3$, $Cu/ZnO$, $Cu/ZnO/Al_2O_3$, $CuO/CoO$, $CuO/CoO/Al_2O_3$, Co/S, Mo/S, Co/Mo/S, $Rh/Ti/SiO_2$, $Rh/Mn/SiO_2$, $Rh/Ti/Fe/Ir/SiO_2$, Rh/Mn/MCM-41, Ni/S, Ni/Mo/S, Ni/Co/Mo/S, and any of the foregoing in combination with Mn and/or V. Again, any of these catalysts can (but do not necessarily) include one or more basic promoters.

The composition of catalysts in reactors 105 and 120, or reaction zones 110 and 125, can be similar or even the same. Reference to a "first catalyst" and "second catalyst" in conjunction with reaction zones is a reference to different physical materials, not necessarily a reference to different catalyst compositions. In some embodiments, a certain type of catalyst is loaded into both reaction zones but, over time, the nominal composition of these catalysts could diverge somewhat due to different exposure conditions.

Product stream 130 output from reactor 120 may comprise, in some variations, about 0% to about 50% methanol, about 10% to about 90% ethanol, about 0% to about 25% CO, about 0% to about 25% $H_2$, and about 5% to about 25% $CO_2$, as well as other gases. In some embodiments, product stream 130 also comprises one or more higher alcohols, such as propanol or butanol.

Referring again to FIG. 1, in some variations unreacted syngas in product stream 130 is separated from product stream 130 to form feedstream 135 and recycled through reactor 120 to further increase, for example, the yield of ethanol and/or other desired products. Alternatively, or in addition, in some variations unreacted syngas in product stream 130 is recycled through reactor 105 by adding it to syngas feedstream 100. The latter approach may be unsuitable, however, if the unreacted syngas in product stream 130 is contaminated, for example, with sulfur, sulfur compounds, metals, or other materials that can poison methanol catalysts in reactor 105.

Also, in some variations a methanol feedstream 140 is added to intermediate product stream 115 or otherwise introduced to reactor 120 to further increase, for example, the yield of ethanol and/or other desired products. For example, methanol in product stream 130 may be separated (not shown) from product stream 130 to form feedstream 140 and then recycled through reactor 120. Methanol from other sources may be introduced, as well or instead, into reactor 120.

In some variations, one or more catalysts in reactor 105, one or more catalysts in reactor 120, or one or more catalysts in both reactor 105 and reactor 120 catalyze the conversion of $CO_2$ to methanol. Production of methanol in reactor 105, reactor 120, or in both reactors may be thereby enhanced by consumption of $CO_2$ present in syngas feedstream 100. Consequently, in some variations, $CO_2$ is added to syngas feedstream 100 or the production and/or subsequent conditioning of syngas feedstream 100 is controlled to produce syngas having a desirable amount of $CO_2$. Suitable catalysts for converting $CO_2$ to methanol may include, in some variations, one or more of those listed above for use in reactor 105 and reactor 120. Enhanced production of methanol by consumption of $CO_2$ may result, in some variations, in enhanced production of ethanol by conversion of the methanol to ethanol and/or by a resulting favorable adjustment of the $H_2/CO$ ratio in the syngas stream introduced to reactor 120.

Figure 2:
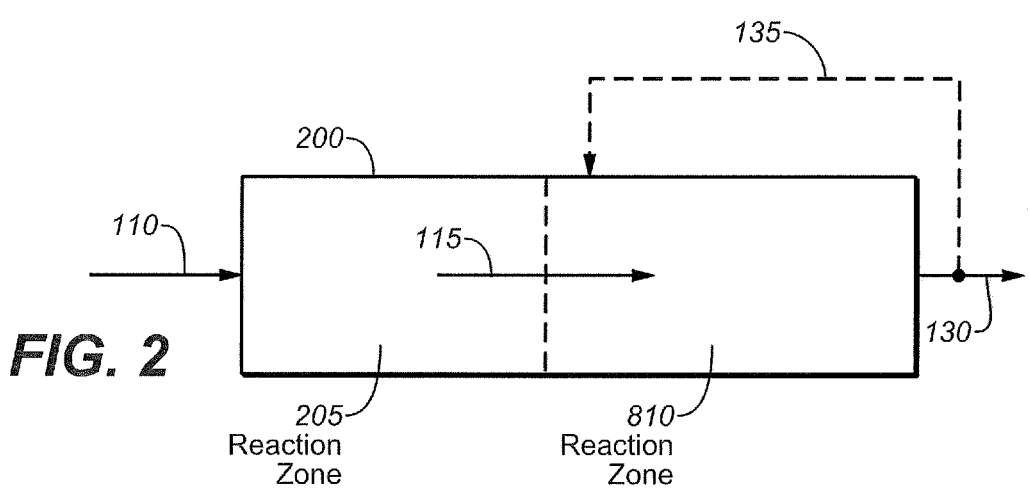
FIG. 2 shows a process flow for producing methanol and ethanol from syngas using two reaction zones in sequence in a single reactor, according to one variation.

Referring now to FIG. 2, some alternative variations differ from those described above primarily by use of a single reactor 200 comprising a first reaction zone 205 and a second reaction zone 810 rather than two reactors. Syngas feedstream 100 is introduced into first reaction zone 205, wherein one or more catalysts convert at least a portion of syngas feedstream 100 to methanol to provide intermediate product stream 115 comprising at least a portion of the unreacted syngas from feedstream 100, methanol, and, in some variations, higher alcohols and/or other reaction products. At least a portion of intermediate product stream 115 is introduced into second reaction zone 810, where one or more catalysts convert at least a portion of syngas from intermediate product stream 115 and/or at least a portion of methanol from intermediate product stream 115 to provide product stream 130 comprising ethanol and, in some variations, methanol, higher alcohols, other reaction products, and/or unreacted syngas from intermediate product stream 115.

Reactor 200 may be any type of suitable catalytic reactor comprising two or more reaction zones. Operation of reactor 200 may be similar to the operation of reactors 105 and 120 described above. In particular, in some variations, the catalysts used in reactions zones 205 and 810 and the operating conditions for the reaction zones are the same as or similar to those for, respectively, reaction zones 110 and 120 described above. The compositions of intermediate product stream 115 and product stream 130 may, in some variations, be the same as or similar to those for the variations described above with respect to FIG. 1. Syngas in product stream 130 may be recycled through reaction zone 810 or added to feedstream 100. $CO_2$ may be added to syngas feedstream 100 or the production and/or subsequent conditioning of syngas feedstream 100 may be controlled to produce syngas having a desirable amount of $CO_2$ for enhanced methanol production. A methanol feedstream (not shown) may be introduced to reaction zone 810 to further increase, for example, the yield of ethanol and/or other desired products. This methanol feedstream may be separated from product stream 130, for example.

Similarly to the two-reactor variations, in some of the single-reactor variations the $H_2/CO$ ratio in intermediate product stream 115 can affect the yield of ethanol and other products in reaction zone 810. In some variations, the $H_2/CO$ ratio of intermediate product stream 115 differs from that of feedstream 100 and provides a higher ethanol yield in reaction zone 810 than would the $H_2/CO$ ratio of feedstream 100. In such variations, production of methanol in reaction zone 205, for example, improves the $H_2/CO$ ratio of the syngas fed to reaction zone 810 from the standpoint of ethanol yield in reactor 120.

Figure 3:
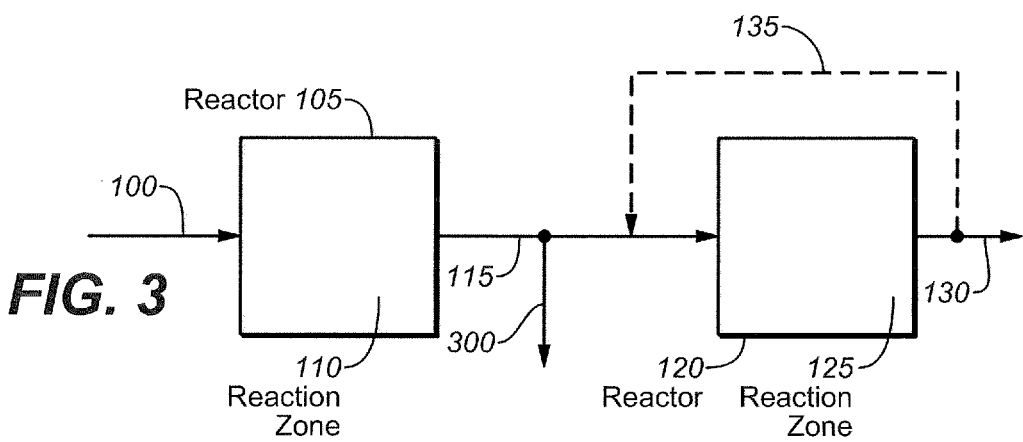
FIG. 3 shows a process flow for producing methanol and ethanol from syngas using two reactors in sequence, with some or all of the methanol produced in the first reactor diverted from the second reactor, according to one variation.

Referring now to FIG. 3, some alternative variations differ from those described with respect to FIG. 1 in that at least a portion (some or substantially all) of the methanol in intermediate product stream 115 is diverted into a methanol product stream 300 prior to the introduction of product stream 115 into reactor 120. Methanol in product stream 300 can be separated and purified by conventional methods. Similarly as above, in some of these variations, the $H_2/CO$ ratio of intermediate product stream 115 differs from that of feedstream 100 and provides a higher ethanol yield in reactor 120 than would the $H_2/CO$ ratio of feedstream 100. Hence, the production of methanol in reactor 105 may advantageously enhance ethanol production in reactor 120 in some of these variations.

In some variations methanol is produced at high yield in a first reactor and subsequently converted to ethanol in a second reactor. One example is described with reference to FIG. 4 described in more detail below.

Figure 5:
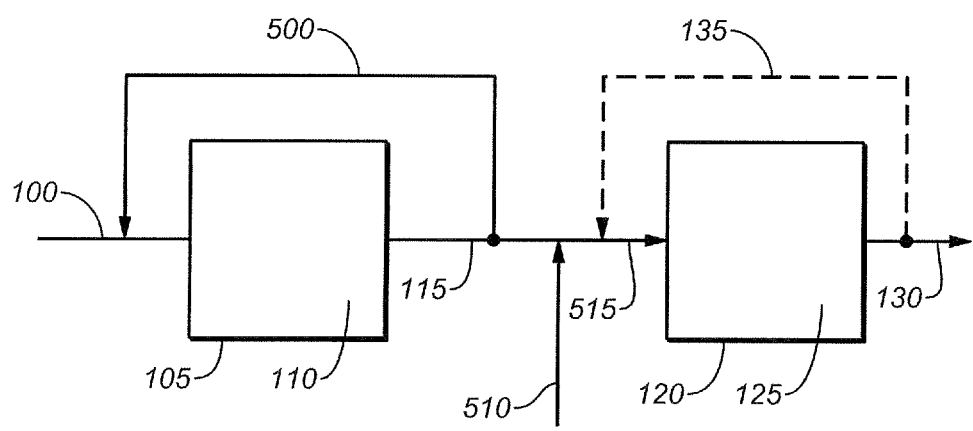
FIG. 5 shows a process flow for producing methanol and ethanol from syngas using two reactors in sequence, with the first reactor producing methanol in high yield for conversion to ethanol in the second reactor, according to one variation.

Referring to FIG. 5, for example, in some variations a syngas feedstream 100 is catalytically converted to methanol in a first reactor 105 at a yield (mole conversion of CO to methanol) of, for example, at least about 50%, preferably at least about 75% or even higher. Such high methanol yields may be facilitated, for example, by separating out some or substantially all of the non-methanol components in intermediate product stream 115 as a stream 500 that is recycled through reactor 105.

An unrecycled portion of intermediate product stream 115, rich in methanol, is (optionally) mixed with another syngas feedstream 510 to provide feedstream 515 which is introduced into reactor 120. At least a portion of the methanol and (optionally) syngas introduced into reactor 120 is catalytically converted to provide a product stream 130 comprising ethanol and, in some variations, methanol, higher alcohol, other reaction products, and/or unreacted syngas from feedstream 515. In some variations, unreacted syngas in product stream 130 is recycled through reactor 120 as feedstream 135 and/or recycled through reactor 105. Various components of product stream 130 may be separated out and/or purified as described above.

In some variations, the ratio of methanol to CO in feedstream 100 may be adjusted, for example, to optimize the yield of ethanol in reactor 120. In some embodiments, the molar ratio of methanol/CO in reactor 120 is between about 0.5 to about 2.0. In particular embodiments, the ratio of methanol/CO in reactor 120 is about 1.0.

Any suitable catalyst or combination of catalysts may be used in reactor 105. Suitable catalysts for reactor 105 may include, but are not limited to, the methanol catalysts listed above. Similarly, any suitable catalyst or combination of catalysts may be used in reactor 120. Suitable catalysts for reactor 120 may include, but are not limited to, the ethanol catalysts listed above. The composition of catalysts in reactors 105 and 120 can be similar or even substantially the same.

In variations of any of the methods described herein that use a first reaction zone and a second reaction zone, the initial syngas stream can be introduced into both the first reaction zone and the second reaction zone. In some embodiments, the syngas is from an external source. In some embodiments, the syngas is from any of the methods described herein (such as residual syngas from a first reaction zone or a second reaction zone).

In some embodiments of any of the methods described herein, syngas from any source is added to the first reaction zone and/or the second reaction zone. In some embodiments of any of the methods described herein, methanol from any source is added to the second reaction zone.

Certain embodiments employ a plurality of physical reactors in one or both of the reaction zones. For example, the first zone could consist of two reactors, followed by a single reactor as the second zone. Or, in another example, the first zone could be one reactor followed by two reactors in the second zone. In general, any "zone" or "reaction zone" can contain a fraction of one, two, three, or more physical reactors.

In some embodiments of any of the methods described herein, reaction conditions (such as the temperature and pressure) used for the conversion of syngas to methanol, the conversion of syngas and/or methanol to ethanol, or the homologation of methanol to ethanol are the same as those described in any of U.S. Pat. Nos. 4,371,724; 4,424,384; 4,374,285; 4,409,405; 4,277,634; 4,253,987; 4,233,466; and 4,171,461; all of which are incorporated by reference herein in their entirety.

Figure 4:
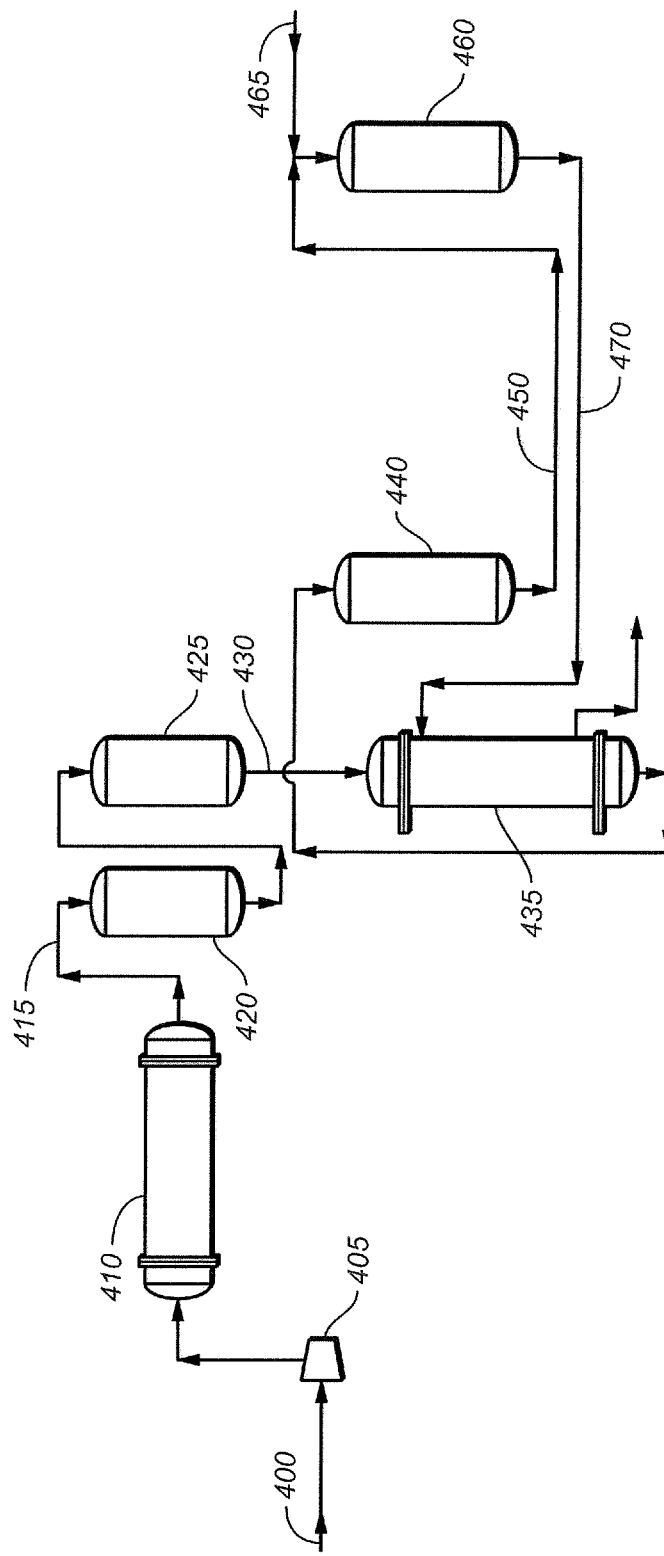
FIG. 4 shows a process flow for producing methanol and ethanol from syngas using two reactors in sequence according to another variation.

FIG. 4 shows an example of a process in which syngas is catalytically converted to methanol in a first reactor, and methanol and residual syngas from the first reactor are converted to ethanol in a second reactor. Referring now to FIG. 4, a single two-stage intercooled reciprocating compressor 405 compresses syngas feedstream 400 to about 1500 psig and feeds it at a temperature of about 135° F. to syngas preheater 410. Preheater 410 is a shell and tube heat exchanger that uses steam as an enthalpy source.

In this example associated with FIG. 4, heated syngas 415 from preheater 410 is sent to a set of reactor guard beds 420, 425. Guard beds 420, 425 are configured in a permanent lead-lag arrangement but are piped such that either bed can be bypassed. The piping arrangement allows one bed to be in service while the other is being regenerated or activated. Regeneration is initiated by a mixed hydrogen and nitrogen line (not shown). Guard beds 415, 420 remove, for example, sulfurs and metals that may poison the methanol catalysts. In some embodiments, one or more catalyst poisons are removed by adsorption over copper, copper chromite, nickel, cobalt, or molybdenum. These and other metals can be supported on high-surface-area refractory inorganic oxide materials such as alumina, silica, silica/alumina, clays, or kieselguhr. One exemplary material is copper on alumina. Exit gases 430 from guard beds 420, 425 are sent to an alcohol reactor cross exchanger 435 at about 350° F. and are heated to about 480° F. during heat exchange with crude alcohol exit gases 470 from second alcohol reactor 460.

With continuing reference to FIG. 4, syngas at about 1500 psig and about 480° F. enters a first alcohol synthesis reactor 440, where at least a portion of the syngas undergoes a catalyzed reaction in supported-catalyst tubular reactors within the reactor vessel. In some variations, the catalyst in reactor 440 is a Cu/ZnO/alumina catalyst. Methanol is expected to be formed via the reaction $CO+2H_2 \rightarrow CH_3OH$. As noted earlier in this detailed description, in some variations methanol may be formed by the hydrogenation of $CO_2$ as well.

Product gases 450 leave alcohol synthesis reactor 440 at a temperature of about 500° F. and enter alcohol synthesis reactor 460. In addition, a methanol stream 465 (e.g., a methanol recycle stream separated from crude alcohol stream 470) is mixed with the product gases 450 from reactor 440 and also introduced to reactor 460. Reactions occurring in reactor 460 can include ethanol formation.

Crude alcohol stream 470 exits reactor 460 at a temperature of about 650° F. and is cooled by heat exchange in alcohol reactor cross exchanger 435 to a temperature of about 530° F. Subsequent heat recovery and other cooling steps (not shown) cool crude alcohol stream 470 to about 100° F. Ethanol, methanol, residual syngas, and other components of crude alcohol stream 470 may be separated and (optionally) purified by using the methods described herein or using conventional methods (not shown). Syngas recovered from stream 470 may, for example, be recycled through the reactors by mixing it with syngas feedstream 400.

Some variations may employ microwave, radio frequency, laser, and/or UV energy in addition to or instead of conventional process heat (e.g., steam, heat from burners, waste heat, etc.) to facilitate the production of ethanol. For example, microwave, radio frequency, laser, and/or UV energy may be used in some variations to convert $CO_2$ in syngas to CO and $O_2$ for more efficient catalytic conversion to methanol and/or ethanol. In some embodiments, a conventional method for converting $CO_2$ in syngas to CO (e.g., treating syngas with a catalyst that promotes the conversion of $CO_2$ to CO) is used for more efficient catalytic conversion to methanol and/or ethanol. In some embodiments, both a catalyst and irradiation (such as irradiation with microwave, radio frequency, laser, and/or UV energy) are used to convert $CO_2$ to CO. In particular embodiments, $CO_2$ is removed from the syngas and irradiation (such as irradiation with microwave, radio frequency, laser, and/or UV energy) and/or a catalyst (such as a thermal catalyst) is used to generate $O_2$ from CO. The $O_2$ is removed and the CO is added to the first and/or second reactor zone. In some embodiments, the irradiation allows a lower temperature and/or pressure to be used for conversion of $CO_2$ to CO than the standard temperatures and pressures used for conversion of $CO_2$ to CO without irradiation. $CO_2$ in syngas stream 100 may be optionally converted in this manner in some variations.

As another example, microwave, radio frequency, laser, and/or UV energy may be used to accelerate the catalytic conversion of syngas to methanol and/or ethanol, and/or to accelerate the catalytic conversion of syngas and/or methanol to ethanol in variations of the processes described above for conversion of syngas to ethanol. More generally, in some variations, microwave, radio frequency, laser, and/or UV energy may be used to accelerate the catalytic conversion of syngas of any origin to methanol and/or ethanol, and/or to accelerate the catalytic conversion of syngas and/or methanol of any origin to ethanol.

In some embodiments, microwave, radio frequency, laser, and/or UV energy is used to irradiate syngas and/or the first catalyst in the first reaction zone to enhance the conversion of syngas to methanol. In some embodiments, the irradiation increases molecular vibrations, increases the energy density, or otherwise activates the syngas and/or first catalyst. Such use of microwave, radio frequency, laser, and/or UV energy in a syngas-to-methanol reactor, for example, may allow the reactor to be operated at lower temperatures and pressures than otherwise.

In some variations, microwave, radio frequency, laser, and/or UV energy is used to irradiate the syngas, methanol, and/or the second catalyst in the second reaction zone. In some embodiments, the irradiation increases molecular vibrations, increases the energy density, or otherwise activates the syngas, methanol, and/or second catalyst. Enhancement of catalytic conversion of methanol to ethanol may occur, for example, by preferential absorption of the microwave, radio frequency, laser, and/or UV energy by the methanol allowing high energy densities to be achieved in the methanol reactants. For example, microwaves heat methanol at a faster rate than ethanol, thereby favoring the conversion of methanol to ethanol. Such use of microwave, radio frequency, laser, and/or UV energy in a methanol to ethanol reactor, for example, may allow the reactor to be operated at lower temperatures and pressures than otherwise.

In some embodiments, methods involve introducing syngas into a reaction zone (e.g., a reactor) comprising at least one catalyst, and irradiating the syngas and/or the catalyst in the reaction zone with energy (e.g., microwave, radio frequency, laser, and/or UV energy). At least a portion of the syngas can be converted to ethanol. The method may also produce methanol or other alcohols. Suitable catalysts may include, but are not limited to, any of the catalysts described herein. In some embodiments, the catalyst is a conventional catalyst for the conversion of syngas to ethanol in one reaction zone or one reactor. In some embodiments, the catalyst favors the formation of ethanol over methanol in the absence of irradiation, and the irradiation enhances the selectivity for the formation of ethanol. For example, the irradiation may heat methanol at a faster rate than ethanol, thereby favoring the conversion of methanol to ethanol. In some embodiments, the catalyst favors the formation of methanol over ethanol in the absence of irradiation, and the irradiation causes the catalyst to produce a lower ratio of methanol to ethanol than in the absence of irradiation. For example, irradiation may cause the catalyst to now produce more ethanol than methanol.

In other embodiments, methods involve introducing syngas and/or methanol into a reaction zone comprising at least one catalyst, and irradiating the syngas, methanol, and/or the catalyst in the reaction zone with energy (e.g., microwave, radio frequency, laser, and/or UV energy). At least a portion of the syngas and/or methanol is converted to ethanol. The method may also produce other alcohols. In particular embodiments, both syngas and methanol are introduced in to the reaction zone. In some embodiments, either syngas or methanol is introduced in to the reaction zone. In some embodiments, methanol is produced using any of the methods described herein or obtained from any other source, and the methanol without syngas is introduced in to the reactor zone. Suitable catalysts may include, but are not limited to, any of the catalysts described herein.

In some embodiments, ethanol is purified from the product stream 130 or crude alcohol stream 470 by first drying the product stream 130 or crude alcohol stream 470 to produce an intermediate product and then distilling the intermediate product to produce a purified ethanol product. In some embodiments, the product stream 130 or crude alcohol stream 470 comprises ethanol, methanol, propanol, butanol, and water. In some embodiments, product stream 130 or crude alcohol stream 470 includes one or more of the following alcohols: 1-propanol, 2-propanol, 1-butanol, 2-butanol, t-butanol, pentanols, hexanols, heptanols, and octanols, and/or higher alcohols. In some embodiments, product stream 130 or crude alcohol stream 470 includes one or more aldehydes, ketones, and/or organic acids (such as formaldehyde, acetaldehyde, acetic acid, and the like).

In particular embodiments, the amount of the ethanol is between about 25% to about 95% of the product stream 130 or crude alcohol stream 470 by weight, such as between about 30% to about 50% or between about 50% to about 90% by weight. In particular embodiments, the amount of the methanol is between about 1% to about 50% of the product stream 130 or crude alcohol stream 470 by weight, such as between about 5% to about 25% or between about 25% to about 55% by weight. In particular embodiments, the amount of the water is between about 1% to about 50% of the product stream 130 or crude alcohol stream 470 by weight, such as between about 1% to about 10%, or about 10% to about 20%. In particular embodiments, the amount of the propanol is between about 0.5% to about 10% of the product stream 130 or crude alcohol stream 470 by weight, such as between about 1% to about 2% or between about 2% to about 8% by weight. In particular embodiments, the butanol is between about 0.2% to about 5% of the product stream 130 or crude alcohol stream 470 by weight, such as between about 0.5% to about 2% or between about 2% to about 5% by weight.

In particular embodiments, the combined amount of ketones and aldehydes is between about 0.1% to about 10% of the product stream 130 or crude alcohol stream 470 by weight, such as between about 0.5% to about 2%. In particular embodiments, the combined amount of organic acids is between about 0.1% to about 10% of the product stream 130 or crude alcohol stream 470 by weight, such as between about 0.5% to about 2%. In particular embodiments, the combined amount of $C_5$ and higher alcohols is between about 0.1% to about 5% of the product stream 130 or crude alcohol stream 470 by weight, such as between about 0.5% to about 2%.

In particular embodiments, drying is performed prior to distillation, rather than after distillation. A drying step can reduce the amount of water in the product stream 130 or crude alcohol stream 470 by at least 75%, preferably at least 90%, more preferably at least 95%, and most preferably at least about 99%. In particular embodiments, the amount of the water is less than or equal to about 1% or less of the intermediate product by weight. Drying can also be referred to as "dehydration" which herein means removal of water from solution, not removal of water at the molecular level (such as during olefin formation).

In some embodiments, the drying step involves passing the product stream 130 or crude alcohol stream 470 through a membrane, such as zeolite membrane, or through one or more molecular sieves to produce an intermediate product. In some embodiments, the molecular sieve has an effective pore size of less than about 5 Angstroms. In certain embodiments, the molecular sieve has an effective pore size of about 3 Angstroms.

In other embodiments, the drying step involves passing the product stream 130 or crude alcohol stream 470 through a desiccant. A large variety of desiccants are known. For example, desiccants can be selected from $SiO_2$, CaO, $CaCO_3$, $CaCl_2$, $CuSO_4$, or $CaSO_4$.

Conventional distillation methods, well-known in the art, can be used to distill the intermediate product. Any number of distillation columns may be employed, depending on the desired overall separation. In some embodiments, ethanol is between about 95% to about 99.9% of the purified product by weight. The purified ethanol product can be made to meet the ASTM D4806-07a specification for fuel ethanol, or some other fuel-grade specification as will be appreciated.

The purified ethanol product can be used to power an internal combustion engine to power a transportation vehicle. In some embodiments, the purified ethanol product can be combined (blended) with at least one other hydrocarbon, or multiple hydrocarbons such as gasoline, to create a liquid-fuel blend.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are incorporated herein by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of purifying one or more alcohols selected from the group consisting of methanol, ethanol, propanol, and butanol, said method comprising the steps of (a) drying an initial mixture comprising methanol, ethanol, propanol, butanol, and water to produce an intermediate product; and then (b) distilling said intermediate product to produce one or more purified alcohols, wherein the amount of water in said initial mixture is between about 1% and about 50% by weight, wherein step (a) removes at least 75% of the water present in said initial mixture and wherein the amount of water in said intermediate product is less than about 5% by weight.

2. The method of claim 1, wherein the amount of ethanol in said initial mixture is between about 25% and about 95% by weight.

3. The method of claim 1, wherein the amount of methanol in said initial mixture is between about 0.1% and about 50% by weight.

4. The method of claim 1, wherein said amount of said water in said intermediate product is less than about 0.5% by weight.

5. The method of claim 1, wherein step (a) removes at least 95% of the water present in said initial mixture.

6. The method of claim 1, wherein step (a) comprises passing said initial mixture through a membrane.

7. The method of claim 6, wherein said membrane is a zeolite membrane.

8. The method of claim 1, wherein step (a) comprises passing said initial mixture through a desiccant.

9. The method of claim 8, wherein said desiccant is selected from the group consisting of $SiO_2$, CaO, $CaCO_3$, $CaCl_2$, $CuSO_4$, and $CaSO_4$.

10. The method of claim 1, wherein step (a) comprises passing said initial mixture through a molecular sieve.

11. The method of claim 10, wherein said molecular sieve has an effective pore size of less than about 5 Angstroms.

12. The method of claim 11, wherein said molecular sieve has an effective pore size of about 3 Angstroms.

13. The method of claim 1, wherein one of said purified alcohols is ethanol.

14. The method of claim 1, wherein one of said purified alcohols is 1-propanol.

15. The method of claim 1, wherein one of said purified alcohols is 1-butanol.

16. The method of claim 1, wherein said distilling produces a purified methanol product and a purified ethanol product.

17. The method of claim 1, wherein said distilling produces a purified methanol product, a purified ethanol product, and a purified 1-propanol product.

18. The method of claim 13, wherein the ethanol concentration of said purified ethanol is between about 95% and about 99.9% by weight.

19. The method of claim 13, wherein said purified ethanol meets the ASTM D4806-07a specification for fuel ethanol.

20. The method of claim 1, further comprising powering an internal combustion engine, at least in part, with said one or more purified alcohols.

21. The method of claim 1, further comprising combining said one or more purified alcohols with at least one other hydrocarbon, thereby creating a liquid-fuel blend.

22. The method of claim 21, further comprising powering an internal combustion engine, at least in part, with said liquid-fuel blend.

23. A method of producing a purified alcohol selected from the group consisting of methanol, ethanol, propanol, and butanol, said method comprising the steps of:
    (a) devolatilizing a carbon-containing feed material to form a gas phase and a solid phase in a devolatilization unit;
    (b) passing said gas phase and said solid phase through a heated reaction vessel to form syngas;
    (c) converting said syngas to a mixture comprising ethanol, methanol, propanol, butanol, and water;
    (d) drying said mixture to produce an intermediate product; and
    (e) distilling said intermediate product to produce a purified alcohol;

wherein step (d) reduces the amount of water in said mixture by at least 95% and wherein the amount of water in said intermediate product is less than about 5% by weight.

24. The method of claim 23, wherein said amount of water in said intermediate product is less than about 0.5% by weight.

25. The method of claim 23, wherein step (d) comprises passing said mixture through a zeolite membrane.

26. The method of claim 23, wherein step (d) comprises passing said mixture through a desiccant.

27. The method of claim 23, wherein step (d) comprises passing said mixture through a molecular sieve.

\* \* \* \* \*